United States Patent [19]

Kato et al.

[11] 4,133,965
[45] Jan. 9, 1979

[54] PROCESS FOR PRODUCING TRICYCLO(5,2,1,0$^{2,6}$)-3-DECENE-8 (OR 9)-OL

[75] Inventors: Mitsuharu Kato; Toru Kikuchi; Takayuki Saito, all of Hitachi, Japan

[73] Assignee: Hitachi Chemical Company, Ltd., Japan

[21] Appl. No.: 829,475

[22] Filed: Aug. 31, 1977

[30] Foreign Application Priority Data

Sep. 8, 1976 [JP] Japan ................................. 51-107569

[51] Int. Cl.$^2$ ........................ C07C 29/04; C07C 29/00
[52] U.S. Cl. ................................................. 568/723
[58] Field of Search ........................ 260/617 F, 617 H; 568/733

[56] References Cited

U.S. PATENT DOCUMENTS

| | | | |
|---|---|---|---|
| 3,345,419 | 10/1967 | Tinsley et al. | 260/617 F |
| 3,849,505 | 11/1974 | Turner | 260/617 F |
| 3,947,500 | 3/1976 | Kollar | 260/617 H |

OTHER PUBLICATIONS

"J.A.C.S.", 67, 723 (1945).

*Primary Examiner*—Norman Morgenstern
*Attorney, Agent, or Firm*—Craig & Antonelli

[57] ABSTRACT

Tricyclo(5,2,1,0$^{2,6}$)-3-decene-8 (or 9)-ol is prepared by hydration of dicyclopentadiene using a heteropoly acid as a catalyst.

12 Claims, No Drawings

PROCESS FOR PRODUCING TRICYCLO(5,2,1,0$^{2,6}$)-3-DECENE-8 (OR 9)-OL

BACKGROUND OF THE INVENTION

This invention relates to a process for hydrating dicyclopentadiene, i.e., tricyclo(5, 2, 1, 0$^{2, 6}$)-deca3,8-diene, (hereinafter referred to as "DCPD" which is a registered trade-mark of Hitachi Chemical Co., Ltd.) to yield the corresponding alcohol, i.e., tricyclo(5, 2, 1, 0$^{2,6}$)-3-decene-8 (or 9)-ol (hereinafter referred to as "DCPD-OH").

DCPD-OH is an alicyclic unsaturated secondary alcohol, and generally so-called as hydroxy dicyclopentadiene, which is used as a modifier for polyester resins, alkyd resins and the like.

Heretofore, DCPD-OH has been prepared by indirect hydration of DCPD by sulfuric acid. For example, there is disclosed a so-called sulfuric acid method in J. Am. Chem. Soc. 67, 723 (1945). The sulfuric acid method, however, has many defects as follows:

(1) Since 20 to 40% sulfuric acid is used, corrosion of the apparatus is remarkable. (2) Since sulfuric acid is mixed in the oil layer obtained by the reaction containing DCPD-OH, the purified DCPD-OH obtained by direct distillation of the oil layer contains a trace of sulfuric acid which makes the product easily colored. In order to avoid coloring of the product, the oil layer is neutralized with an alkali and washed. But these treatments produce a large amount of waste water. Thus a large amount of investment is necessary to avoid water pollution. (3) In the sulfuric acid method, since a stoichiometric amount of sulfuric acid is necessary for the starting DCPD, and since sulfuric acid should be used 2 to 4 times (by weight) as much as the starting DCPD if the concentration of sulfuric acid is 20 to 40%, a reaction kettle having a large volume should be used.

In addition, because of complicated procedures as mentioned above, the production cost of DCPD-OH is inevitably very high. Further if sulfuric acid is used as a catalyst, polymers are by-produced, which lowers selectivity for DCPD-OH. Therefore production of DCPD-OH by direct hydration with high selectivity and without causing water pollution has been desired in this industry.

On the other hand, in general, as catalysts for hydrating unsaturated compounds, there are known mineral acid catalysts such as phosphoric acid, boric acid, and their salts as well as sulfuric acid mentioned above, and heteropoly acid catalysts. The mineral acid catalysts are known to have such a defect as remarkable corrosion of the apparatus and there is the same problem in the production of DCPD-OH. It is known that the heteropoly acid catalysts can be used for the hydration of olefins having up to 4 carbon atoms, particularly for ethylene and propylene, from which the corresponding alcohols can be obtained in good yields. But if the number of carbon atoms of olefins become larger, for example in the case of diisobutylene and myrcene, reactions hardly proceed or no reactions take place even if the heteropoly acid catalysts are used.

But surprisingly, the present inventors have found that hydration reaction can be proceeded by a heteropoly acid in the case of DCPD having the norbornene skeleton having 10 carbon atoms and accomplished the present invention.

SUMMARY OF THE INVENTION

It is an object of this invention to provide a process for producing DCPD-OH by a simple method. It is another object of this invention to provide a process for producing DCPD-OH by a closed system without causing a problem of disposal of waste water. It is a further object of this invention to provide a process for producing DCPD-OH with excellent selectivity.

This invention provide a process for producing DCPD-OH which comprises reacting dicyclopentadiene with water using a heteropoly acid as a catalyst.

DETAILED DESCRIPTION OF THE INVENTION

In most cases, the desired DCPD-OH is obtained as a mixture of 8-ol and 9-ol.

Examples of the heteropoly acids are silicotungstic acid, phosphotungstic acid, silicomolybdic acid, phosphomolybdic acid, and the like, which are water soluble.

Among them, tungsten heteropoly acids such as silicotungstic acid, phosphotungstic acid, and the like are preferable because of high catalytic activity.

The catalyst is used in an amount of 0.05 to 10% by weight based on the weight of the water used. Compared with the amount of sulfuric acid in the case of the sulfuric acid method, the hydration reaction in this invention can be carried out with by far little amount of the catalyst. The heteropoly acid catalyst is usually used in the form of an aqueous solution.

The molar ratio of water to DCPD ($H_2O$/DCPD) is usually in the range of 1 to 20, preferably 5 to 15. If the molar ratio is too small, production of tar increases due to heat polymerization of DCPD and selectivity for DCPD-OH is lowered. If the molar ratio is too large, a reactor having a large volume should be used.

The reaction of this invention is usually carried out at a temperature of 50° to 200° C., preferably 100° to 150° C. Heating is preferably carried out with sufficient stirring. If the reaction temperature is too low, the hydration reaction proceeds very slowly and thus it takes a long reaction time. On the other hand, if the reaction temperature is too high, heat polymerization of DCPD easily takes place.

Any pressure may be employed, if the pressure is the same or higher than the water vapor pressure at the reaction temperature. Therefore, when the reaction is carried out at 80° C. or more, it is preferable to compress the reactor with inert gas such as nitrogen.

After the reaction, the reaction solution is easily separated into two layers, the upper water layer of which contains the water and the catalyst and the lower oil layer of which contains DCPD-OH produced. The oil layer separated can be used for distillation as it is to give the desired product, DCPD-OH, without alkali neutralization and washing, unlike the sulfuric acid method. The separated water layer containing the catalyst is recovered and can be used again as a part or whole of the water and the catalyst. By these reasons, the apparatus for producing DCPD-OH according to this invention can employ a closed system. There is no problem of disposing waste water and the procedure can easily be simplified. Therefore the process of this invention is very advantageous economically compared with the sulfuric acid method.

This invention is illustrated by way of the following Examples, in which all percents are by weight unless otherwise specified.

EXAMPLE 1

In a vertically agitating type autoclave having an inner volume of 200 cc, a catalyst solution obtained by dissolving 1.6 g of silicotungstic acid ($SiO_2.12\ WO_3.\ 26\ H_2O$) in 36.0 g of deionized water was placed and then 52.8 g (0.4 mole) of DCPD was added thereto. Inner pressure of the autoclave was made 40 kg/cm$^2$ by nitrogen gas. The reaction was carried out at 150° C. for 4 hours. After the reaction, the lower oil layer containing DCPD-OH was taken out from the reaction solution by a separating funnel. The oil layer was distilled under reduced pressure to recover 23.8 g of unreacted DCPD and to give 23.0 g of a fraction having boiling point of 140° C./30 mmHg (DCPD-OH). Conversion of DCPD was 55% and selectivity for DCPD-OH was 69.7%.

EXAMPLE 2

The process of Example 1 was repeated except for using phosphomolybdic acid ($P_2O_5.24\ MoO_3.63\ H_2O$) in place of silicotungstic acid. Conversion of DCPD was 5% and selectivity for DCPD-OH was 70%.

EXAMPLE 3

To the aqueous catalyst solution separated from the reaction solution of Example 1, deionized water was added to give 36.0 g of the catalyst solution. The resulting catalyst solution and 52.8 g of DCPD were placed in an autoclave. The reaction was carried out at 150° C. for 4 hours under 40 kg/cm$^2$ of nitrogen. Conversion of DCPD was 39% and selectivity for DCPD-OH was 31%.

EXAMPLE 4

In a vertically agitating type autoclave having an inner volume of 200 cc, a catalyst solution obtained by dissolving 1.6 g of phosphotungstic acid ($P_2O_5.24\ WO_3.63\ H_2O$) in 36.0 g of deionized water was placed and then 52.8 g (0.4 mole) of DCPD was added thereto. Inner pressure of the autoclave was made 40 kg/cm$^2$ by nitrogen gas. The reaction was carried out at 150° C. for 4 hours. Conversion of DCPD was 33% and selectivity for DCPD-OH was 77.3%.

COMPARATIVE EXAMPLE 1

In a flask, 26.4 g (0.2 mole) of DCPD and 86.0 g of 25% sulfuric acid aqueous solution were placed. The air in the flask was replaced by nitrogen and the flask was sealed. The reaction was carried out at 100° C. for 5 hours. The reaction solution was separated into an oil layer and an aqueous sulfuric acid solution layer by a separating funnel. The oil layer was neutralized by a 5% sodium carbonate aqueous solution, washed with deionized water and distilled under reduced pressure. Conversion of DCPD was 61% and selectivity for DCPD was 55%.

COMPARATIVE EXAMPLE 2

The process of Example 1 was repeated except for using 0.75 mole of diisobutylene, 3 moles of water, and reaction conditions of reaction temperature of 130° C. and pressure of 5 atmospheres. No hydrate of diisobutylene was obtained.

As mentioned above, this invention has the following features:

(1) Since heteropoly acids are used as a catalyst contrary to sulfuric acid and the like of the conventional methods, the amount of the catalyst can be reduced very remarkably. (For example, sufficient amounts of catalysts by weight are sulfuric acid/DCPD = 0.81 in the case of the sulfuric acid method, while silicomolybdic acid/DCPD = 0.03 in the case of this invention.)

(2) Neutralization and washing procedures of the oil layer containing DCPD-OH produced before purification by distillation are not necessary. Therefore, there arises no problem of disposal of waste water.

(3) The catalysts used in the process of this invention do not corrode the apparatus unlike sulfuric acid.

What is claimed is:

1. A process for producing tricyclo (5, 2, 1, 0$^{2,6}$)-3-decene-8(or 9)-ol which comprises reacting dicyclopentadiene with water in the presence of a sufficient amount, to catalyze the reaction, of a heteropoly acid as a catalyst, under a pressure which is the same or higher than the water vapor pressure at a temperature at which the reaction is taking place.

2. A process according to claim 1, wherein the heteropoly acid is a tungsten heteropoly acid.

3. A process according to claim 2, wherein the tungsten heteropoly acid is phosphotungstic acid or silicotungstic acid.

4. A process according to claim 1, wherein 1 to 20 moles of water per mole of dicyclopentadiene is used.

5. A process according to claim 1, wherein 0.05 to 10% by weight of heteropoly acid based on the weight of water is used.

6. A process according to claim 1, wherein the reaction is carried out at a temperature of from 50° to 200° C.

7. A process according to claim 4, wherein the temperature at which the reaction takes place is 50° C. to 200° C.

8. A process according to claim 7, wherein said temperature is between 100° to 150° C.

9. A process according to claim 7, wherein, after the reaction, the resulting mixture is separated into a water layer containing water and the catalyst and an oil layer containing tricyclo (5, 2, 1, 0$^{2,6}$)-3-decene-8(or 9)-ol.

10. A process according to claim 9, wherein the separated oil layer is distilled to separate the tricyclo (5, 2, 1, 0$^{2,6}$)-3-decene-8(or 9)-ol.

11. A process according to claim 9, wherein the separated water layer containing water and the catalyst is recovered and used with a further amount of dicyclopentadiene in order to form a further amount of tricyclo (5, 2, 1, 0$^{2,6}$)-3-decene-8(or 9)-ol, whereby a closed system having no waste water to be removed from the system is achieved.

12. A process according to claim 1, wherein the heteropoly acid is an acid selected from the group consisting of silicomolybdic acid and phosphomolybdic acid.

* * * * *